United States Patent [19]
Martin et al.

[11] Patent Number: 5,829,445
[45] Date of Patent: Nov. 3, 1998

[54] METHODS FOR LASER TREATMENT OF TISSUE

[75] Inventors: Steve W. Martin, Ames; Gerald J. Shirk, Cedar Rapids, both of Iowa

[73] Assignee: Iowa State University Research Foundation, Inc., Ames, Iowa

[21] Appl. No.: 458,883

[22] Filed: Jun. 2, 1995

Related U.S. Application Data

[60] Division of Ser. No. 209,002, Mar. 10, 1994, which is a continuation-in-part of Ser. No. 950,913, Sep. 24, 1992, abandoned.

[51] Int. Cl.$^6$ .................................................. A61B 19/00
[52] U.S. Cl. ......................... 128/898; 606/16; 385/142
[58] Field of Search ........................ 606/2, 3, 9, 13–16; 128/898; 385/141, 142, 143; 65/385, 387, 390, 392

[56] References Cited

U.S. PATENT DOCUMENTS

| | | |
|---|---|---|
| 2,326,059 | 8/1943 | Nordberg . |
| 3,958,058 | 5/1976 | Elmer . |
| 4,122,853 | 10/1978 | Smith . |
| 4,126,136 | 11/1978 | Auth et al. . |
| 4,170,997 | 10/1979 | Pinnow et al. . |
| 4,183,621 | 1/1980 | Kao et al. . |
| 4,184,860 | 1/1980 | Schneider . |
| 4,209,229 | 6/1980 | Rittler . |
| 4,273,109 | 6/1981 | Enderby . |
| 4,367,013 | 1/1983 | Guerder et al. . |
| 4,398,790 | 8/1983 | Righini . |
| 4,592,353 | 6/1986 | Daikuzono . |
| 4,662,368 | 5/1987 | Hussein et al. . |
| 4,693,244 | 9/1987 | Daikuzono . |
| 4,702,759 | 10/1987 | Roba . |
| 4,729,373 | 3/1988 | Peyman . |
| 4,736,743 | 4/1988 | Daikuzono . |
| 4,832,979 | 5/1989 | Hoshino . |
| 4,867,776 | 9/1989 | Sharp . |
| 4,883,337 | 11/1989 | Dahlgren . |
| 4,932,989 | 6/1990 | Presby . |
| 5,037,174 | 8/1991 | Thompson . |
| 5,067,975 | 11/1991 | Backer et al. . |
| 5,100,501 | 3/1992 | Cholewa . |
| 5,119,461 | 6/1992 | Beyer et al. . |
| 5,154,744 | 10/1992 | Blackwell et al. . |
| 5,188,652 | 2/1993 | Goldenberg . |
| 5,196,005 | 3/1993 | Doiron et al. . |
| 5,212,762 | 5/1993 | Shimada et al. . |
| 5,282,798 | 2/1994 | Bruse et al. ............................. 606/16 |
| 5,348,552 | 9/1994 | Nakajima et al. ...................... 606/13 |
| 5,416,878 | 5/1995 | Bruce ...................................... 606/16 |
| 5,491,767 | 2/1996 | McPherson et al. .................... 606/15 |

FOREIGN PATENT DOCUMENTS

| | | |
|---|---|---|
| 60-42716 | 3/1985 | Japan . |
| 63-103843 | 5/1988 | Japan . |
| 63-313103 | 12/1988 | Japan . |
| 2244650 | 12/1991 | United Kingdom . |

OTHER PUBLICATIONS

Corning Incorporated Brochure entitled "ULE™ Titanium silicate Code 7971", Dec. 1990.

R.C. DeVries et al., "The System $TiO_2$–$SiO_2$" *Trans. Brit. Ceram. Soc.*, 53, 525–540 (1954).

K. Kamiya et al., "$TiO_2$–$SiO_2$ glasses prepared from metal alkoxides", *J. Mater. Sci.*, 15, 2937–2939 (1980).

(List continued on next page.)

*Primary Examiner*—Michael Peffley
*Attorney, Agent, or Firm*—Mueting, Raasch & Gebhardt, P.A.

[57] ABSTRACT

A new optical fiber and method of manufacturing the same developed for use with surgical laser systems. The fiber core utilizes an ultra-low expansion (ULE) material. The preferred ULE fiber consists of silicon dioxide core doped with titanium dioxide which is cladded and jacketed for chemical and abrasion resistance. The resulting fiber is stable against degradation due to thermal expansion.

14 Claims, 3 Drawing Sheets

OTHER PUBLICATIONS

P.C. Schultz, "Binary titania–Silica Glasses Containing 10 to 20 Wt% $TiO_2$", *J. Am. Ceramic Society*, 59, 214–219 (Jun. 1976).

H. Ito et al., "Single–mode optical fibers", *Chem. Abs.*, 109, Abstract No. 114984y (Oct. 3, 1988).

R. Th. Kersten et al., "Laser Beam Delivery System for Medical Applications" in *Optical Fibers in Medicine;* A. Katzir, Ed.; SPIE Optical Engineering Press: Bellingham, Washington; pp. 395–398 (Jan. 1990).

W.T. Minehan et al., "Titania–Silica Glasses Prepared by Sintering Alkoxide Derived Spherical Colloids", *J. Non–Crystalline Solids*, 108, 163–168 (Mar. 1989).

Anther Laboratories Graph of Linear Expansion (1988).

S. Ashley et al., "Thermal Characteristics of Sapphire Contact Probe Delivery Systems for Laser Angioplasty", *Lasers in Surgery and Medicine*, 10, 234–244 (1990).

M.W. Berns et al., "Laser Applications in Biomedicine", *J. Laser Applications*, 34 (Fall 1988).

G. Biamino et al., "Laser in Medicine", *Advances in Laser Medicine I, First German Symposium on Laser Angioplasty*, 45 (1987).

J. Brumsted et al., "A Second Puncture Probe for Laparoscopic Delivery of the Nd:YAG Laser", *Obstertrics & Gynecology*, 73, 672 (Apr. 1989).

J.R. Brumsted et al., "Expanding GYN Applications of the Nd:YAG Laser", *Contemporary OB/GYN*, 34, 31 (Oct. 15, 1989).

Fiber Optic Laser Systems.

S. Hessel et al., "Possibilities for the Use of Nd:YAG Laser in Vascular Recanalization", *Advances in Laser Medicine I, First German Symposium on Laser Angioplasty*, 89 (1986).

S.N. Joffe, "Contact Neodymium: YAG Laser Surgery in Gastroenterology: A Preliminary Report", *Lasers in Surgery and Medicine*, 6, 155–157 (1986).

N. Kaikuzone, "Computer Controlled Contact Nd:YAG Laser System for Interstitial Local Hyperthermia", *Laser in Medicine*, 712, 34 (1986).

J. Lammer et al., "Experimental and Clinical Results with Neodymium: YAG Laser Angioplasty", *Advances in Laser Medicine I, First German Symposium on Laser Angioplasty*, 96 (1986).

M. Moretti, "A Status Report on Lasers in Medicine", *Laser Focus/Electro Optics*, 88 (Apr. 1987).

P.C. Schultz et al., "Ultra–Low–Expansion Glasses and Their Structure in the $SiO_2$–$TiO_2$ System" in *Glasses and the Vitreous State;* J. Zarzycki, Ed.; Cambridge University Press: Cambridge; pp. 453–461 (1991).

R.S. Scott, "Surgical Applications of the Sapphire Contact Probe and the Nd:YAG Laser", *Optical and Laser Technology in Medicine*, 605 (Jan. 1986).

G. Shirk et al., "Contact Surgery with Sculptured Quartz Fibers Using an Nd:YAG, Argon, or KTP Laser: Alteration of Lateral Thermal Damage Effects by Variation of Fiber Tip Geometry at Low Laser Power Output".

G. Shirk et al., "Contact Surgery with Sculptured Quartz Fibers Using an Nd:YAG, Argon, or KTP Laser: Thermal Damage Effects Caused by Power Variation".

G.J. Shirk, "Use of the ND:YAG Laser for the Treatment of Endometriosis", *Am. J. Obstertrics and Gynecology*, 160, 1344–1351 (Jun. 1989).

G. Shirk e tal., "Operative Laparoscopy with the Nd:YAG Laser in the Treatment of Endometriosis and Pelvic Adhesions" *Lasers in Surgery and Medicine*, 11, 297–300 (1991).

G.J. Shirk et al., "Comparison of Tissue Effects with Sculptured Fiberoptic Cables and Other Nd:YAG Laser and Argon Laser Treatments", *Lasers in Surgery and Medicine*, 11, 563–568 (1991).

B.J. Skutnik et al., "High Strength, Hard–Coated All Silica Optical Fiber for Laser Surgery", *Optical Fibers in Medicine IV*, 1067, 211 (1989).

S. Suzuki et al., "Experimental Study and Clinical Application of New Ceramic Endoprobe with Nd–YAG Laser; Endoscopic Hemostatis, Pyloroplasty and Cutting Biopsy", *Lasers in Medicine*, 712, 2 (1986).

S. Suzuki et al., "Experimental Studies of Endoscopic Local Hyperthermia with Contact Nd:YAG Laser", *Lasers in Medicine*, 712, 15 (1986).

METHODS FOR LASER TREATMENT OF TISSUE

RELATED APPLICATIONS

This is a division of application Ser. No. 08/209,002, filed Mar. 10, 1994, which is a continuation-in-part of application Ser. No. 07/950,913, filed Sep. 24, 1992 (now abandoned).

STATEMENT REGARDING GOVERNMENT RIGHTS

The present invention was made with government support from the U.S. Department of Commerce under Grant No. ITA 87-02. The Government may have certain rights in this invention.

FIELD OF THE INVENTION

The present invention relates to the field of laser fibers. More particularly, the present invention relates to laser fibers constructed of ultra-low-expansion (ULE) materials and methods of making such fibers.

BACKGROUND OF THE INVENTION (Throughout this Specification, there appear numbered superscripts. These refer to prior art references listed by number in the "Other Documents" portion of the "Information Disclosure Statement" that accompanied the parent application identified above.)

For many years, lasers have been used for a variety of surgical procedures. The desired effects may be thermal, photodisruptive or photo-chemical. Lasers may be delivered to and targeted on the treatment site by either a free beam system using mirrors or by directing the laser light in an optical fiber. Optical fibers have been the preferred system of laser delivery for surgical procedures, if the desired wavelength can be transmitted through the fiber. In a non-contact mode, the optical fiber has no effect on the wavelength specific tissue effect.

Most lasers currently used for medical-surgical procedures are used for their thermal effect which is dependent upon the specific way the laser light energy is transferred to thermal energy in the tissue. A common laser used is the carbon dioxide ($CO_2$) laser whose wavelength at 10.6 $\mu$m makes it opaque to cellular water. The $CO_2$ laser is therefore totally absorbed by water and rapidly converted to thermal energy over a very short distance (<100 $\mu$m).

Recently, Nd:YAG laser systems, coupled to silica fibers with either sculptured or bare tips or with sculptured sapphire tips, have shown great benefits as surgical tools when used for certain procedures.[1–6] Using these laser systems with a bare fiber, photocoagulation to tissue depths of 4 to 5 mm in tissue can be attained in a non-contact mode.[6–12] In a contact mode, incision and cauterization of the nearby tissue can be achieved.[13–20]

These two capabilities, though providing the surgeon with new and powerful tools in performing procedures that are very close to being hemostatic, have as yet to be integrated into a full spectrum of laser optical fiber surgical systems. At one extreme, only photocoagulation can be achieved in a non-contact mode while at the other extreme only incision can be achieved in a contact mode. Between these two extremes, there is a range of combined and controlled photocoagulation and incision that would be highly desirable, and a fiber optic system that could provide this full-spectrum capability would provide the surgeon with a broad range of new surgical capabilities to meet the specific needs of a broad range of surgical procedures.

The most common optical fiber material used for the delivery of laser light energy at the present time is silica glass. Indeed, the same glass chemistry presently used in all optical fibers for laser surgery is also used in telecommunication optical fibers. These optical fiber cables are capable of transmitting laser light through very small diameters and they can be threaded to almost any part of the body creating little or no damage to surrounding normal tissue. These fiber optic delivery systems are, therefore, ideal for use with endoscopy.

Such silica fibers have been shown to be highly effective in photocoagulating tissue in a non-contact mode. However, when these fibers come into contact with tissue or blood there is significant thermal-mechanical damage to the fiber and disruption of light transmission. This disruption limits the focusing of the laser and causes the laser energy incident upon the damaged optical fiber tip to be converted into thermal heating of the tip. Hence, after the degradation of the optical fiber tip has begun, the fiber can no longer be used for photocoagulation.

When the fiber optic cable contacts tissue, there is a marked change in the tissue response and a significant reduction in the tissue transmission of the laser light. Because of the absorption of laser energy at the optical fiber tip at the tissue contact surface, the fiber is rapidly heated to high temperatures thereby destroying the optical quartz fiber. The effect on the surrounding tissue is variable and has an unpredictable tissue damage pattern.

The thermal-mechanical breakdown of the optical fiber that follows the use of the fiber in a contact mode also results in the contamination of the incisional site with silica glass fragments. These fragments may present a bio-hazard as their effect on tissue has not been fully studied. Perhaps more importantly, the use of a technique for precise laparoscopic dissection that creates a variable tissue effect with significant lateral coagulation is less than optimal.

Sapphire tips have been used in an attempt to incise tissue without destruction of the optical fiber. Examples of this approach are found in Daikuzono U.S. Pat. No. 4,693,244 and Hoshino U.S. Pat. No. 4,832,979.

Sculptured sapphire tips range in shapes from long small-angle cones, to shorter sharper-angle cones, to blunt end cylinders to rounded semi-spheres. It is believed that by changing the angle at the end of the sapphire tip, the focusing or defocusing of the laser light can be achieved; small, sharp angles tending to focus the light down to smaller angles whereas larger angles, such as the rounded semi-sphere ends, tending to defocus the laser light. The belief is that by changing this angle, the nature of the tissue response can be changed from incision at the highly focused extreme to photocoagulation at the defocused extreme.

Although this effect of focusing and defocusing may be the case when the optical fiber is used in non-contact, it is likely not the case when used in the contact mode. Rather it is our experience that with the sapphire tips, the energy transmission from the fiber to the tissue is dominated by the contact surface between the tissue and the sapphire tip. As with the optical fiber, for a short time, the sapphire tip will lase in contact with the tissue but then it breaks down and the tip will only incise the tissue in a manner similar to that of the silica fiber tip. The sapphire tip, however, due to its single crystal structure, when heated by the laser fails catastrophically along well-defined crystallographic planes. Hence, rather than small pieces or flakes of the sapphire tip coming off the tip in a gradual manner as is the case with the silica optical fiber, the sapphire tip cracks along the entire length of the tip and large chunks of the tip fall off into the surrounding tissue area. Such failure is catastrophic in the sense that these larger pieces of sapphire (typically 1–2 mm×1–2 mm) are quite hot due to the laser heating and when they contact the tissue, they cause thermal damage to surrounding normal tissue in the surgical area and must be retrieved from the site.

Another failure mechanism of fibers with sapphire tips is that because they are composite systems, the sapphire tip must be connected to the optical fiber cable. The most common method of attachment includes a small brass ferrule compression fitted onto the teflon protective jacket of the fiber. Because the sapphire is a good thermal conductor, the brass ferrule is heated along with the sapphire tip and, in some instances of continued use, melts the teflon jacket and falls off into the surgical area. In this case, both the sapphire tip and the brass ferrule can burn the tissue at the surgical site. As a result, both the sapphire tip and brass ferrule must be retrieved from the surgery site before the damage to the tissue is extensive. Hence, as with the silica fibers, the sapphire tips degrade and contaminate the surgery tissue site when used in a contact mode.

Other attempts at providing fibers for contact laser surgery have been directed to coating the fiber tip with infrared absorbing material, as taught in Daikuzono U.S. Pat. No. 4,736,743, or, in a manner similar to that used in sapphire contact tips, changing the tip configuration to modify the laser beam and reduce localized heating at the tip. These attempts have not met with success because, even though they are specifically designed for contact applications, they suffer from the same thermal expansion and eventual degradation described above for the silica fiber tips and sapphire tipped fibers.

The use of laser energy in the blue-green region of the electromagnetic spectrum to incise tissue provides advantages in tissue with a high hemoglobin concentration (usually indicated in tissue with high degrees of vascularity such as the liver). The absorption of such energy is increased by the high iron content of such regions. These systems also use simple and inexpensive silica optical fiber delivery system. One important disadvantage is that these systems are typically used only in non-contact procedures. Presumably, these silica-based laser systems would suffer the same thermal-mechanical break down as do the Nd:YAG laser fiber systems if used in contact procedures.

Although some of the fibers described above can provide adequate performance when used in non-contact applications to accomplish photocoagulation, the reality facing surgeons is that contact between the fiber tips and tissue is extremely difficult to avoid due to the close quarters in which these devices operate. Once the fiber or sapphire tip contacts tissue and degradation of the tip surface occurs. After the initial degradation occurs, the performance (for either photocoagulation or incision) of the fiber can no longer be accurately predicted by the surgeon. If predictable characteristics are required, a new fiber tip must be created, either by cutting and polishing a new tip (a laborious, time consuming process) or by replacing the entire fiber. Both of these options increase the cost of the laser surgery.

In summary, the laser optical fiber systems currently in use, silica or otherwise, remain useful as photocoagulating or incisional tools only so long as they are used in non-contact procedures. Given the close nature of the environments in which these devices operate, however, contact and the resulting degradation are difficult, if not impossible, to avoid. As such, there is a need for a fiber material which provides predictable operating characteristics in either a contact or non-contact mode and which can be modified to provide a predictable balance between photocoagulation and contact incision.

SUMMARY OF THE INVENTION

The present invention provides a fiber optic cable with a core formed of ULE materials which exhibits predictable characteristics regardless of its use in methods involving non-contact, contact or a combination of both. As a result, fibers according to the present invention are useful for photocoagulation, incision (contact or non-contact) or a combination of photocoagulation and incision.

Because of the extremely low expansion coefficients of the ULE materials, fibers according to the present invention retain their integrity and, as a result, their characteristics such as energy transmission/absorbance far longer than fibers constructed of conventional materials.

Furthermore, because the ULE material does not degrade rapidly when heated, it can be intentionally processed to absorb a predetermined percentage of laser energy at the tip, thus providing a useful thermal incision device, in addition to providing a consistent, predetermined percentage of laser energy for photocoagulation. The energy absorption is preferably accomplished by doping the fiber tip with an absorbing specie, such as a colored transition metal ion which provides a desired level of energy absorption. That predetermined level of energy absorbance can be used to control the extent of the input laser energy that is used to incise tissue. If no dopant were added to the tip, then substantially all of the laser energy incident on the tip would be transmitted to the tissue and complete photocoagulation would result. If the tip were doped with a laser absorbing specie then a fraction of laser energy would be absorbed at the fiber contact tip and the tip would be heated to a temperature that would be proportional to the level of doping in the tip. Lightly doped tips will incise tissue lightly and heavily doped tips will incise tissue heavily. In the extreme of doping, substantially all of the laser energy would be absorbed at the fiber tip and the result would be a 100% incisional fiber tip.

Although fully incisional fiber tips already exist (i.e., those fibers which have suffered thermal-mechanical breakdown either by using tissue or the commonly used practice of degrading the fiber with a wooden tongue blade), the benefit with the fiber system of the invention is that a fully incisional fiber would be but one of a fill spectrum of such fibers where the extent of photocoagulation or incision is predetermined. Furthermore, the silica fibers in common use must be intentionally damaged to yield this performance and this damage continues so long as the fibers are used, leaving behind a small but measurable residue of glass fragments in and along the tissue incisional site.

In one aspect of the invention, the laser optical fiber comprises ultra-low expansion (ULE) materials, coated with a waveguiding cladding material, typically a UV-curable silicone acrylate polymer, jacketed with a protective polymer, typically teflon, and used with a laser, typically a Nd:YAG laser. Such optical fibers exhibit near zero thermal shock over a wide range of temperatures and as a result remain stable when used in contact with tissue and energized with a laser.

ULE fibers according to the present invention can also be doped or otherwise modified to provide a range of controlled photocoagulation and/or incision of tissue depending upon, for example, the extent of doping with a laser absorbing specie, typically a transition metal ion, like $Fe^{+2}$ or $Fe^{+3}$.

These and various other advantages and features which characterize the invention are pointed out with particularity in the attached claims. For a better understanding of the invention and its advantages, reference should be made to the drawings which form a part hereof, and to the accompanying description, in which various preferred and alternate embodiments and methods according to the present invention are described in more detail.

DESCRIPTION OF THE PREFERRED AND ALTERNATE EMBODIMENTS OF THE INVENTION

According to the principles of the invention, the problem of the optical fiber thermal-mechanically degrading when in contact with tissue is controlled by increasing the thermal shock resistance of the optical fiber. To accomplish this, ULE material fibers are used which, when coated with a hard polymer cladding and jacketed with a tough teflon abrasion and chemical resistant layer, provide a surgical optical fiber that is resistant to thermal shock-induced failure.

Typically, known silica fiber core materials exhibit thermal coefficients of linear expansion of $0.5 \times 10^{-6}/°C$. or greater for working temperatures of 25° to 700° C. Preferred ULE materials according to the present invention, however, exhibit thermal coefficients of linear expansion of less than about $0.5 \times 10^{-6}/°C$. in the same temperature range. The exact coefficients of the ULE materials are, of course, dependent on temperature and the nature of the ULE material being used. At all temperatures, however, ULE materials according to the present invention will exhibit linear thermal coefficients of expansion less than that of silica glass.

The preferred ULE material according to the present invention comprises titania-doped silica glass, variations of which are described in greater detail below. Other ULE materials include, but are not limited to, fibers made of a glass-ceramic containing $Li_2O$, $Al_2O_3$, and $SiO_2$.

Figure 1:
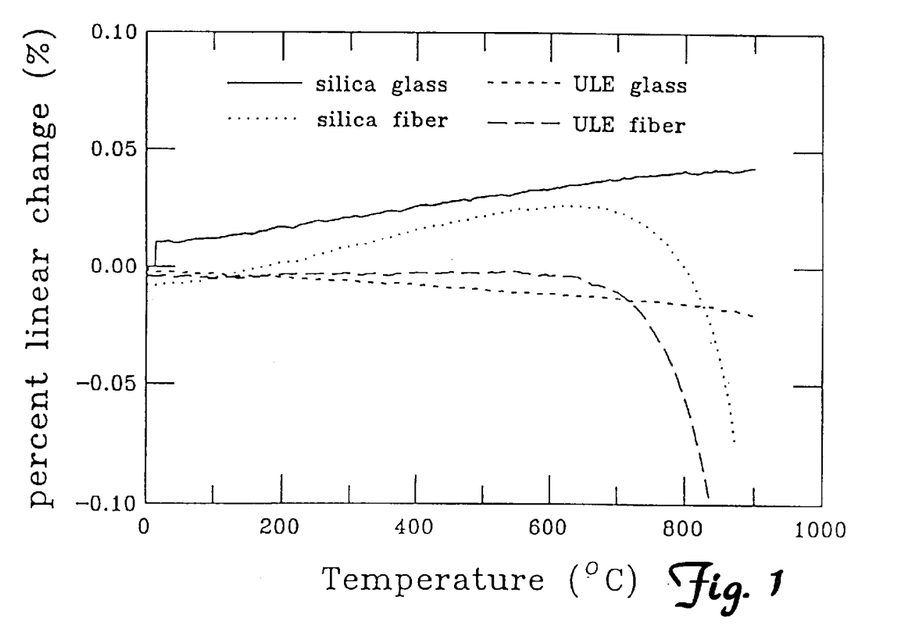
FIG. 1 is a chart showing the percent of linear expansion versus temperature of four different bulk material and fiber specimens.
Figure 2:
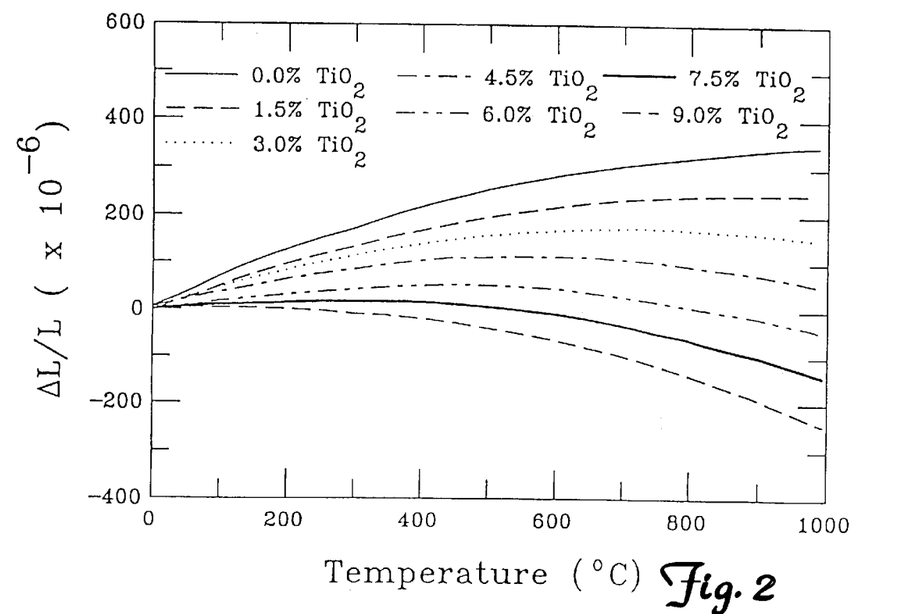
FIG. 2 is a chart showing the fractional linear expansion versus temperature for a series of titania ($TiO_2$) doped silica ($SiO_2$) fibers.

FIGS. 1 and 2 show that silica fibers exhibit substantially larger thermal expansion coefficients than titania-doped ULE silica glasses. FIG. 1 is a chart illustrating the linear expansion of four different bulk glasses and fibers at various temperatures: a silica (quartz) glass rod, a section of a commercial 600 μm silica optical fiber, a titania-doped silica ULE glass rod and a section of ULE ~600 μm optical fiber.

FIG. 1 shows that the ULE glass exhibits a much less expansion than that of the commercial silica. FIG. 1 also shows that the ULE glass exhibits the ULE behavior even in the fiber form. Because thermal stresses across a given fiber generated by a temperature gradient are inversely proportional to the expansion coefficient of the material used to form the fiber, it is expected that such ULE fibers would be much less susceptible to thermal stress failure and as a result tend to remain stable when the fiber is brought into contact with tissue and energized with a laser.

FIG. 2 shows that the thermal expansion of the titania-doped glass decreases substantially as the titania dopant concentration increases from 0 to about 6–8% (weight). FIG. 2 also shows that the titania doping dramatically decreases the linear expansion to the extent that by 6 to 7.5 wt % $TiO_2$, the expansion coefficient is near zero for a wide range of temperatures, up to ~800° C. The slope of each curve shown on FIG. 2 is defined as the expansion coefficient, which determines the thermal shock resistance of the fiber.

Figure 3:
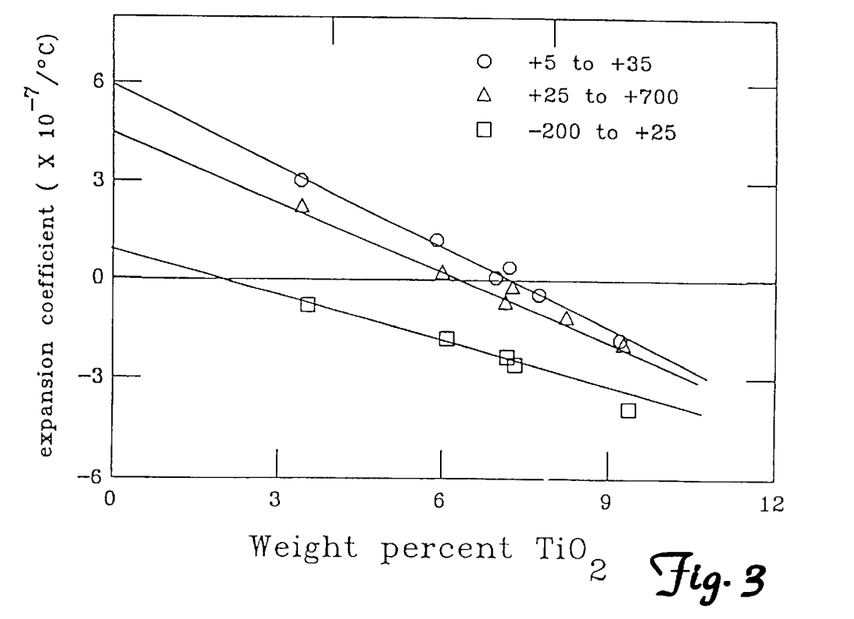
FIG. 3 is a chart showing the average expansion coefficients, defined as the rate of change of the linear expansion with temperature, for three ranges of temperatures, for titania doped silica fibers of different weight percentages.

These slopes are shown on FIG. 3 for three ranges of temperatures, +5° to +35° C., +25° to +700° C., and −200° to +5° C. In the present application, the range of +25° to +700° C. is applicable. FIG. 3 shows that for this range the average expansion coefficient reaches zero (infinite thermal shock resistance) near a doping of 7.5 wt % $TiO_2$. Thus, a glass with this doping would have a thermal shock resistance approaching infinity. Although in practice such values would never be attained, the thermal shock resistance would increase dramatically for glass with a titania-doping level near 7.5 wt %

Figure 4:
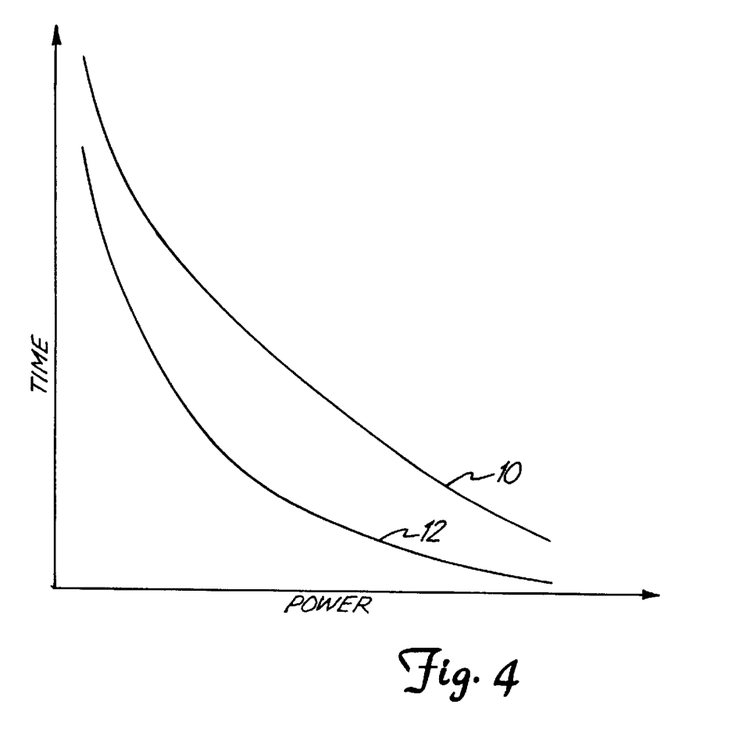
FIG. 4 depicts the relative relationship between fibers according to the present invention and known silica glass fibers when compared on a power vs. time graph indicating stable working regions.

FIG. 4 is a graphic representation of the relative stable working regions (as a function of laser power versus time) of both fibers according to the present invention and known fibers. The working regions of fibers according to the present invention, represented by the area under line 10, provide an increased stable working envelope when compared to the area under line 12, which represents the stable working region of known fibers. As shown in FIG. 4, ULE fibers can be used for longer periods of time and/or at higher power levels (relative to silica glass fibers) without degradation sufficient to substantially affect the performance of the fibers.

It should be noted that FIG. 4 depicts the relationship between lines 10 and 12 in a relative, as opposed to absolute sense. The actual relationship will depend on the characteristics of the tissue in contact with the fibers and other factors. In all cases, however, the stable working limits of ULE fibers according to the present invention will exceed those of known silica fibers.

Because of the stable nature of ULE fibers according to the present invention, they may be intentionally provided in embodiments which absorb a desired, predetermined amount of laser energy which is then converted to heat for incision or other purposes. Known silica fibers would degrade under such conditions, but the low linear thermal coefficients of expansion of ULE materials used in fibers according to the present invention, provide a larger range of thermal stability. Techniques of modifying the fibers to include a means for heating the fiber tip through the absorption of laser energy include, but are not limited to, abrading the fiber tip or doping the tip with a laser absorbing specie.

The preferred method of modifying the ULE fibers to increase energy absorption and decrease transmission of laser energy is doping the fiber tips. The fiber tips can be doped to varying extents with a laser absorbing specie to provide for controlled photocoagulation and/or incision of tissue depending upon the extent of doping of the fiber tip. Fibers which are more heavily doped will absorb more laser energy, converting it into thermal energy at the tip of the fiber. Fibers which are lightly doped, or not doped at all, will absorb less laser energy, thereby passing more energy out of the fiber to provide increased photocoagulation.

Preferably, the laser absorbing specie is a transition metal-ion like $Fe^{+2}$ or $Fe^{+3}$. Other laser absorbing specie can be used in place of the preferred specie. Examples include, but are not limited to: $Co^{+2}$, $Mn^{+2}$ and $Ni^{+2}$.

The preferred method of doping the tip with the laser absorbing specie is to coat the area to be doped, typically the distal end tip, with a solution or slurry containing the dopant. The tip and solution are then heated to about 1000° C. in a small electric furnace. By holding the coated tip at this temperature for a period of time, preferably a few minutes to less than an hour, the dopant will dissolve into the tip causing a homogenous concentration throughout the tip volume. The concentration in the tip is governed by the amount and concentration of dopant placed on the surface of the tip prior to heating.

Alternate methods of doping the ULE fibers according to the present invention will be known to those skilled in the art, including, but not limited to ion implantation, etc.

Figure 5:
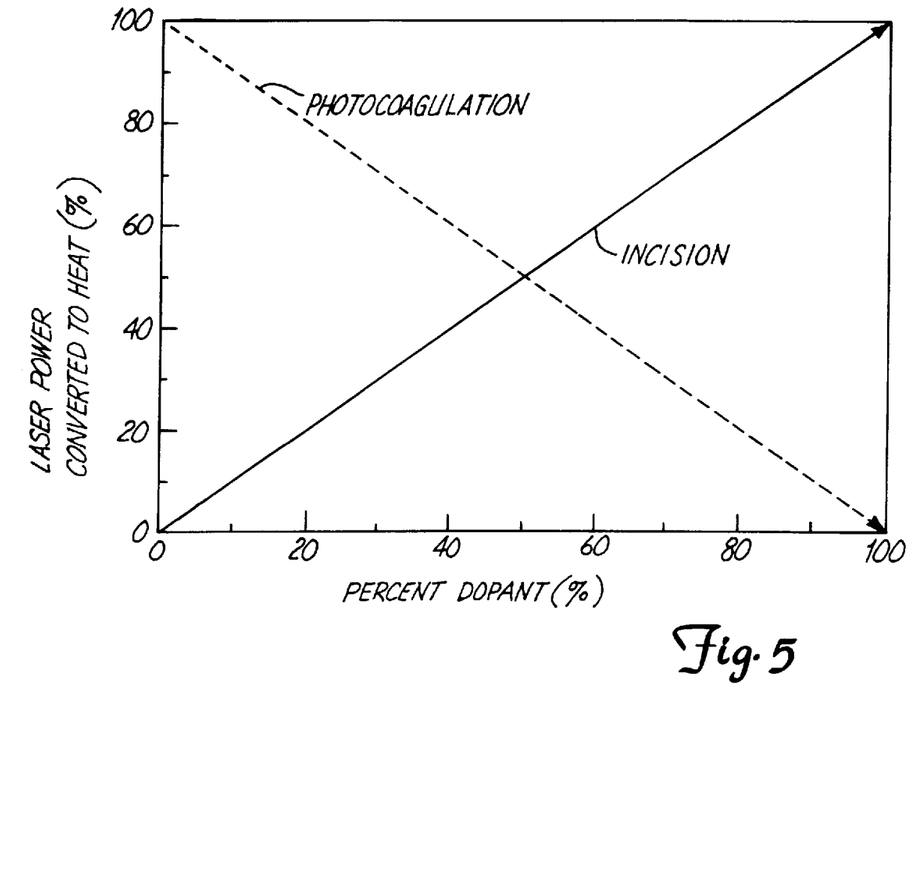
FIG. 5 is a chart showing the range of performance of an optical fiber utilizing the principles of the invention.

FIG. 5 illustrates the range of the performance of various optical fibers produced according to the principles of the invention, which may be used in contact with tissue. At the far left, FIG. 5 depicts the performance of a fiber tip that has no laser absorbing dopant and, as a result, the fiber transmits 100% of the laser energy into the tissue medium. At the far right, FIG. 5 depicts the performance of a fiber tip doped with the maximum amount of the laser absorbing dopant and as a result, the fiber converts 100% of the laser energy into heat at the fiber tip.

Between the two extremes depicted in FIG. 5, a range of dopant concentrations exist where a fraction of the laser energy is converted to heat at the tip and the remaining fraction of laser energy is transmitted through the fiber tip to the time. This characteristic enables the production of a range of different laser optical fibers which can be used to provide a predetermined amount of both photocoagulation and incision depending upon the amount of doping.

In addition to being able to withstand the natural thermal cycling that results from energizing these optical fibers in contact with tissue, ULE optical fibers also have the unique ability to withstand the thermal cycling arising from high peak energy levels in use with rapidly pulsed "Q-switched" laser systems. Whether thermal cycling arises from the tissue contact or from internal heating due to a pulsed laser or a combination of the two or other phenomena, the near zero expansion of the ULE optical fibers makes them uniquely suited for such applications, especially new applications such as photo-disruptive laser therapy and/or surgery.

Such titania-doped silica fibers also are non-toxic, straight forward and inexpensive to prepare, chemically inert, and are optically transparent from the ultraviolet to the infrared.

For these reasons, ULE optical fibers can be produced and fiberized into contact tips for use with all standard laser optical fiber delivery systems. Such fibers would be compatible with all medical laser optical fiber delivery systems using visible and near-infrared laser energy. The diameters of such fibers typically range from 100 to 1000 $\mu$m, with the most common being 600 $\mu$m. These diameters are the most commonly used diameters in practice today. The optical connectors for the tips are standard "SMA" connectors commonly used in laser systems. The fibers can be attached into fiber handholding devices in a fashion commonly in use today. In short, all of the known uses, optical connectors, laser delivery systems and packaging methods are completely compatible with the ULE optical fibers of the invention. In fact, this compatibility is a tremendous advantage.

As is standard in the art and practice and known to those skilled in the art, fibers produced using the principles of the invention are clad with a hard polymer and jacketed with a tough buffer material, typically teflon or tefzel. The preferred cladding is a fluoracrylate material, although other cladding materials can also be used, including, but not limited to silicone acrylate polymers and other materials.

The distal ends of the fibers can be formed into any of a range of different configurations. All such configurations and others commonly used are suitable for use with the ULE optical fibers of the invention when used either in a contact or non-contact mode.

All configurations of the ULE laser optical fibers of the invention are compatible with Nd:YAG, argon-ion, KTP or any other laser system operating between the wavelengths of ≈200 nm to 3000 nm. The preferred ULE laser optical fibers of the invention are compatible with these lasers producing up to ≈120 Watts for a fiber diameter of 600 $\mu$m.

Although the new ULE laser optical fiber of the invention has been developed to be 100% compatible in every way to the pure silica laser optical fiber, it has been found that differences do exist in the way in which the ULE optical fibers are prepared.

In a typical preparation of silica optical fibers, a prepolished pure silica fiber preform glass rod is chucked into a preform holder, inserted into a graphite element argon gas environment furnace, heated up to the fiber drawing temperature, and then pulled into fiber form at a precisely controlled speed and temperature. The pulled fiber is then immediately coated with a hard acrylic protective and waveguiding cladding, tension tested for minimum strength and then wound onto a take up spool. Such fiber drawing practices have been developed over some time, and the ULE fiber drawings is compatible with all of these practices except that the fiber is preferably pulled using an air or oxygen atmosphere furnace.

The air or oxygen atmosphere is required to keep the titanium in the doped preform in its highest ($Ti^{+4}$) oxidation state. If the glass preform is reduced ($Ti^{+4} \rightarrow Ti^{+3}$) then this reduces the fibers' ability to transmit the laser light because of the blue coloring indicative of the $Ti^{+3}$ in the fibers. Such fibers cannot be used as surgical tools because they will not transmit laser energy.

It has been our finding that the commercially available ULE titania-doped silica glass contains reduced titania ($Ti^{+3}$) such that when core-drilled preforms of this glass are pulled, even in oxidizing atmospheres, the fibers are severely colored blue and will not transmit laser energy. This problem makes commercially available ULE glass preforms unusable for fiberizing laser optical fibers.

For this reason, the glass preform must be processed to the proper $Ti^{+4}$ oxidation state before it is pulled into a fiber useable for transmission of laser energy according to the present invention. In one preferred method, annealing the glass preform in air at 1000° C. for periods ranging from 18 to 24 hours, the glass preforms will oxidize to the $Ti^{+4}$ state such that when the fibers are pulled from these annealed preforms they are colorless and will transmit laser light. In an alternate preferred method, the preforms may be annealed for 48–72 hours in an oxygen atmosphere at temperatures of 1000° to 1200° C. before pulling. ULE fibers pulled from preforms treated according to the present invention transmit substantially all of the laser energy directed through them.

Apparently, the $Ti^{+3}$ in the commercially available titania-doped ULE material arises from the manufacturing process, and therefore changes in the process could result in preforms already in the oxidized state. Currently, chemical vapor deposition (CVD) techniques are used to prepare the glass preforms. One such CVD technique is taught in U.S. Pat. No. 2,326,059. These prior art processes do not take special precautions to insure the correct oxidization state of the titanium in the glass and, as a result, typically could not be used to manufacture useable laser fibers. Special precautions are taken only to insure that the titanium is delivered to the reaction chamber in high purity and in the correct stoichiometry. It is believed that the glass preforms produced by known CVD techniques result in substantial amounts of reduced titania, i.e., $Ti^{+3}$. Therefore, to produce glass preforms that can be pulled into fibers suitable for transmission of laser energy, special care must be taken to insure not only high purity and correct stoichiometry, but the correct oxidation state of the titanium as well.

In the methods according to the present invention, pure oxygen is used in the CVD reaction chamber resulting in the oxidation of the $TiCl_4$ and $SiCl_4$ gas streams to $TiO_2$ and $SiO_2$, respectively, thus maintaining suitable levels of $Ti^{+3}$ and $Ti^{+4}$ in the ULE fibers sufficient to allow the transmission of substantially all laser energy directed through the fibers.

Fibers thus produced according to the principles of the invention provide a safe and reliable means of photocoagulating tissue with a laser activated optical fiber without exhibiting the thermal-mechanical breakdown phenomenon common to ordinary silica-based fibers. The fibers of the invention will provide a surgeon using lasers with a stable fiber whose properties and performance do not change throughout a typical laser surgical procedure. The increased stability of the optical fiber of the invention will therefore enable surgeons to perform laser surgery procedures more reliably, controllably and safely than when ordinary silica fibers are used.

The physical, chemical, and optical properties of the titania-doped silica optical fibers of the invention are similar to those of the silica fibers except that they exhibit a slightly higher index of refraction and, as described above, a much lower, near zero, linear coefficient of thermal expansion. The similarities allow them to be used with all the common lasers used in surgery.

The preferred fibers of the invention can also be provided in the same diameters and lengths and use the same optical and surgical connectors and fittings as those of the silica fibers which, combined with the similar optical properties, will allow them to be used completely interchangeably with all the common commercial surgical lasers now being used with the silica-based fibers. The laser-optical fiber-tissue response is also identical to that resulting from the silica-based optical fiber system, except that the titania-doped silica fiber remains stable throughout the surgical procedure. The cost and technical requirements of producing the titania-doped optical fibers of the invention are also very similar to those of the silica fibers. All of these similarities to the silica-based optical fibers of the invention a great improvement in the optical fiber laser surgery technology.

Having thus described the invention in connection with the preferred embodiment thereof, it will be evident to those skilled in the art that various revisions and modifications can be made to the preferred embodiment without departing from the spirit and scope of the invention. It is our intention, however, that all such revisions and modifications as are obvious to those skilled in the art will be included within the scope of the following claims.

What is claimed is:

1. A method for laser treatment of tissue comprising the steps of:
    a) providing a laser fiber having a core constructed of silica-titania glass, the core terminating in a tip; and
    b) transmitting laser energy through the core to treat tissue, wherein the tip retains its integrity during treatment.

2. The method of claim 1, further comprising the step of contacting tissue with the laser fiber tip.

3. The method of claim 1, further comprising the step of incising the tissue with the laser energy.

4. The method of claim 1, wherein the silica-titania glass exhibits a thermal coefficient of linear expansion of less than about $0.5 \times 10^{-6}/°C$. in temperatures from about 25° C. to about 700° C.

5. The method of claim 1, wherein the silica-titania glass is substantially colorless.

6. The method of claim 1, further comprising the steps of:
    a) absorbing laser energy in the core proximate the tip; and
    b) contacting tissue with the tip to thereby incise the tissue.

7. The method of claim 6, wherein the step of absorbing laser energy further comprises providing a laser absorbing dopant in the core proximate the tip.

8. The method of claim 7, further comprising the step of varying the concentration of the laser absorbing dopant to provide a predetermined level of laser energy absorption.

9. The method of claim 1, wherein the step of providing a laser fiber further comprises providing a laser fiber having a core consisting essentially of silica-titania glass.

10. The method of claim 9, wherein the core comprises a concentration of $TiO_2$ of about 7.5 percent by weight.

11. A method for laser treatment of tissue comprising the steps of:
    a) providing a laser fiber having a core of silica-titania glass exhibiting a thermal coefficient of linear expansion of less than about $0.5 \times 10^{-6}/°C$. in temperatures from about 25° C. to about 700° C., the core terminating in a tip; and
    b) transmitting laser energy through the core;
    c) absorbing laser energy in the core proximate the tip;
    d) contacting tissue with the laser fiber tip; and
    e) incising the tissue with the laser energy, wherein the tip retains its integrity during treatment.

12. The method of claim 11, wherein the silica-titania glass is substantially colorless.

13. The method of claim 11, wherein the step of providing a laser fiber further comprises providing a laser fiber having a core consisting essentially of silica-titania glass.

14. The method of claim 13, wherein the core comprises a concentration of $TiO_2$ of about 7.5 percent by weight.

* * * * *

UNITED STATES PATENT AND TRADEMARK OFFICE
CERTIFICATE OF CORRECTION

PATENT NO.: 5,829,445
DATED: November 3, 1998
INVENTOR(S): Steven W. Martin et al.

It is certified that error appears in the above-identified patent and that said Letters Patent is hereby corrected as shown below:

Title page, item [75], inventors: delete "Stève" and insert --Steven--;

Page 2, first column, delete "Anther Laboratories" and insert --Anter Laboratories--;

Page 2, first column, in the Brumsted et al. entry, delete "Obstertrics" and insert --Obstetrics--;

Page 2, second column, in the 4th G. Shirk entry, delete "e tal." and insert --et al.--;

Column 4, line 47, delete "fill" and insert --full--; and

Column 8, lines 49-50, delete "(Ti+3)" and insert --($Ti^{+3}$)--.

Signed and Sealed this

Third Day of October, 2000

Attest:

Q. TODD DICKINSON

*Attesting Officer*   *Director of Patents and Trademarks*